US009335276B2

(12) United States Patent
Van Der Wilt

(10) Patent No.: US 9,335,276 B2
(45) Date of Patent: May 10, 2016

(54) MONITORING METHOD AND APPARATUS FOR CONTROL OF EXCIMER LASER ANNEALING

(71) Applicant: Coherent LaserSystems GmbH & Co. KG, Göttingen (DE)

(72) Inventor: Paul Van Der Wilt, Göttingen (DE)

(73) Assignee: Coherent LaserSystems GmbH & Co. KG, Göttingen (DE)

( * ) Notice: Subject to any disclaimer, the term of this patent is extended or adjusted under 35 U.S.C. 154(b) by 0 days.

(21) Appl. No.: 14/195,656

(22) Filed: Mar. 3, 2014

(65) Prior Publication Data
US 2015/0247808 A1 Sep. 3, 2015

(51) Int. Cl.
*H01L 21/268* (2006.01)
*G01N 21/95* (2006.01)
*H01L 21/66* (2006.01)
*G01N 21/84* (2006.01)
*G01N 21/88* (2006.01)
*G02B 21/00* (2006.01)
*G01N 21/47* (2006.01)
*H01L 21/02* (2006.01)

(52) U.S. Cl.
CPC ........ *G01N 21/9501* (2013.01); *G01N 21/4788* (2013.01); *G01N 21/8422* (2013.01); *G01N 21/8851* (2013.01); *G02B 21/002* (2013.01); *H01L 21/268* (2013.01); *H01L 22/12* (2013.01); *G01N 2021/8461* (2013.01); *G01N 2021/8477* (2013.01); *G01N 2201/10* (2013.01); *H01L 21/02532* (2013.01); *H01L 21/02686* (2013.01)

(58) Field of Classification Search
USPC .......................... 438/437, 478, 482, 487, 488
See application file for complete search history.

(56) References Cited

U.S. PATENT DOCUMENTS

| 4,806,018 A | 2/1989 | Falk |
| 7,061,623 B2 | 6/2006 | Davidson |
| 7,723,169 B2 | 5/2010 | Graefe et al. |
| 2003/0017658 A1 | 1/2003 | Nishitani et al. |
| 2005/0002016 A1 | 1/2005 | Tsao |
| 2007/0173039 A1 | 7/2007 | Tagusa |
| 2009/0002687 A1 | 1/2009 | Wenzel |
| 2013/0341310 A1 | 12/2013 | Van Der Wilt |

FOREIGN PATENT DOCUMENTS

JP 2004-172424 A 6/2004
JP 2013258181 A 12/2013

OTHER PUBLICATIONS

Leonhardt et al., "Removing ambiguities in surface roughness measurement," 1982, Optica Acta, 29(4), 493-499.*

(Continued)

*Primary Examiner* — Jaehwan Oh
*Assistant Examiner* — Bo Bin Jang
(74) *Attorney, Agent, or Firm* — Morrison & Foerster LLP

(57) ABSTRACT

A method is disclosed evaluating a silicon layer crystallized by irradiation with pulses form an excimer-laser. The crystallization produces periodic features on the crystallized layer dependent on the number of and energy density ED in the pulses to which the layer has been exposed. An area of the layer is illuminated with light. A microscope image of the illuminated area is made from light diffracted from the illuminated are by the periodic features. The microscope image includes corresponding periodic features. The ED is determined from a measure of the contrast of the periodic features in the microscope image.

10 Claims, 12 Drawing Sheets

(56) References Cited

OTHER PUBLICATIONS

International Search Report and Written Opinion received for PCT Patent Application No. PCT/EP2013/062883, mailed on Sep. 23, 2013, 9 pages.

International Preliminary Report on Patentability received for PCT Patent Application No. PCT/EP2013/062883 mailed on Dec. 31, 2014, 8 pages.

International Search Report and Written Opinion received for PCT Patent Application No. PCT/EP2015/054326, mailed on May 27, 2015, 10 pages.

* cited by examiner

MONITORING METHOD AND APPARATUS FOR CONTROL OF EXCIMER LASER ANNEALING

TECHNICAL FIELD OF THE INVENTION

The present invention relates in general to melting and recrystallization of thin silicon (Si) layers by pulsed laser irradiation. The method relates in particular to methods of evaluating the recrystallized layers.

DISCUSSION OF BACKGROUND ART

Silicon crystallization is a step that is often used in the manufacture of thin-film transistor (TFT) active-matrix LCDs, and organic LED (AMOLED) displays. The crystalline silicon forms a semiconductor base, in which electronic circuits of the display are formed by conventional lithographic processes. Commonly, crystallization is performed using a pulsed laser beam shaped in a long line having a uniform intensity profile along the length direction (long-axis), and also having a uniform or "top-hat" intensity profile in the width direction (short-axis). In this process, a thin layer of amorphous silicon on a glass substrate is repeatedly melted by pulses of laser radiation while the substrate (and the silicon layer thereon) is translated relative to a delivery source of the laser-radiation pulses. Melting and re-solidification (re-crystallization) through the repeated pulses, at a certain optimum energy density (OED), take place until a desired crystalline microstructure is obtained in the film.

Optical elements are used to form the laser pulses into a line of radiation, and crystallization occurs in a strip having the width of the line of radiation. Every attempt is made to keep the intensity of the radiation pulses highly uniform along the line. This is necessary to keep crystalline microstructure uniform along the strip. A favored source of the optical pulses is an excimer laser, which delivers pulses having a wavelength in the ultraviolet region of the electromagnetic spectrum. The above described crystallization process, using excimer-laser pulses, is usually referred to as excimer-laser annealing (ELA). The process is a delicate one, and the error margin for OED can be a few percent or even as small as ±0.5%

There are two modes of ELA. In one mode, the translation speed of a panel relative to the laser beam is sufficiently slow that the "top-hat portion" of the beam-width overlaps by as much as 95% from one pulse to the next so any infinitesimal area receives a total of about 20 pulses. In another mode referred to as advanced ELA or AELA the translation speed is much faster and in a single pass over a panel the irradiated "lines" have minimal overlap and may even leave un-crystallized space therebetween. Multiple passes are made such that the entire panel is irradiated with a total number of pulses that may be less than in an ELA process to produce equivalent material.

Whichever ELA mode is employed, evaluation of crystallized films on panels in a production line is presently done off line, by visual inspection. This inspection is entirely subjective and relies on highly trained experienced inspectors, who through their experience are able to correlate observed features of the panels with very small changes, for example less than 1%, in energy density in the crystallizing beam. In a manufacturing environment, the process of visual analysis and establishing if a change of process energy density is necessary typically takes between about one and one and one-half hours from when the crystallization was performed, with a corresponding adverse effect on production line throughput of acceptable panels.

There is a need for an objective method of evaluation of the ELA process. Preferably, the method should be capable at least of being implemented on a production line. More preferably, the method should be capable of being used for quasi real-time evaluation in a feedback loop for automatically adjusting process energy density responsive to data provided by the evaluation.

SUMMARY OF THE INVENTION

The present invention is directed to a method and apparatus for evaluating a semiconductor layer at least partially crystallized by exposure to a plurality of laser-radiation pulses having an energy density on the layer, the crystallization producing a first group of periodic surface features on the layer in a first direction, and a second group of periodic features in a second direction perpendicular to the first direction, the form of the first and second groups of periodic features depending on the energy density of the laser-radiation pulses to which the semiconductor layer has been exposed.

In one aspect of the invention a method for evaluating the semiconductor layer comprises illuminating an area of the crystallized semiconductor layer and recording a microscope image of the illuminated area in light diffracted from the illuminated area by the first and second groups of periodic features. The recorded image contains horizontal and vertical groups of periodic image-features corresponding to respectively the first and second groups of periodic features in the illuminated area of the layer. The energy density is determined from a measure of the contrast of at least one of the horizontal and vertical groups of periodic image-features.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain principles of the present invention.

DETAILED DESCRIPTION OF THE INVENTION

Figure 1:
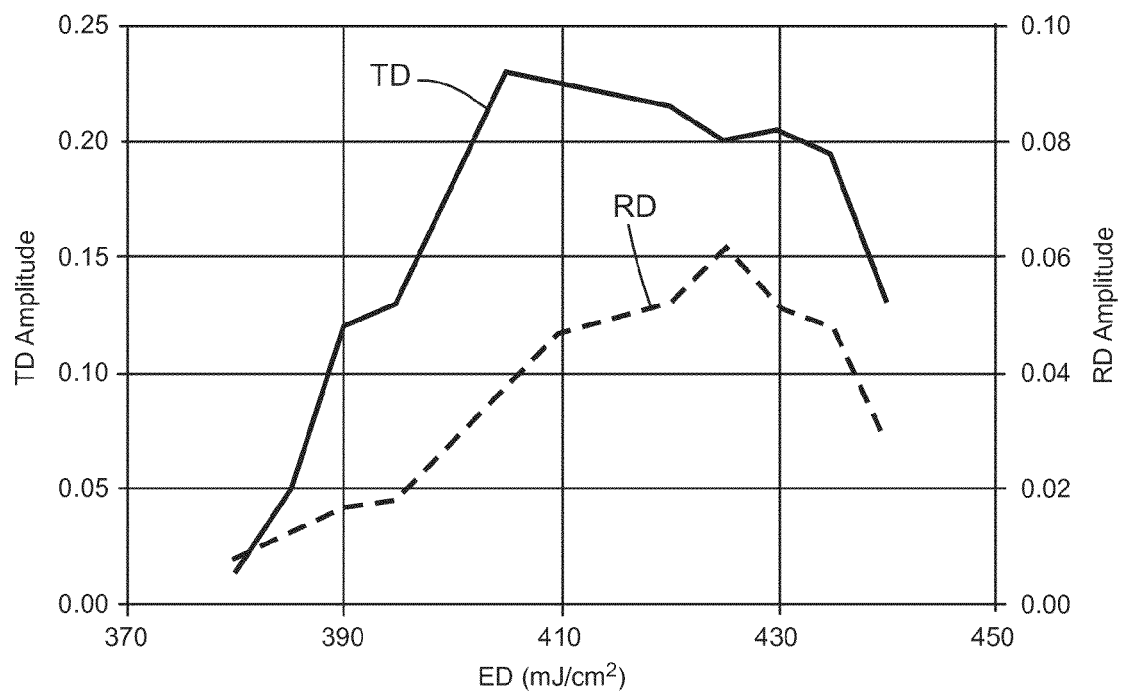
FIG. 1 is a graph schematically illustrating measured peak amplitude as a function of pulse energy density in rolling and transverse direction for fast Fourier transforms (FFTs) of scanning laser microscope images of ELA crystallized silicon layers.

ELA processing of thin Si films leads to formation of surface-roughness protrusions which are formed as a result of the expansion of Si upon solidification. The protrusions are formed especially between three or more solidification fronts colliding during lateral growth. The protrusions are often not randomly located. Rather, they are aligned due to processes of ripple formation collectively referred to in the literature as laser-induced periodic surface structures (LIPSS). The ripples thus consist of series of well aligned protrusions. The ripple formation is only observed within an energy density window (range) in which partial melting of the film is achieved. Typically the ripple periodicity is on the order of the wavelength of the incident light, for example, around 290-340 nm for XeCl excimer lasers. Because of these small dimensions, ripples cannot, or can at best hardly, be resolved using conventional optical microscopy techniques.

What is typically observed in optical bright field microscopy is that the surface of ELA processed films consists of elongated darker colored regions interspersed with brighter regions. Close inspection of the darker regions shows that they consist of more strongly rippled (ordered) regions having higher protrusions, while in between are regions having less order and/or lower protrusions. The more ordered regions are herein referred to as ridges, while the regions in between are referred to as valleys. It is an inventive finding that the formation of ridges appears to be correlated to that of ripples with the typical orientation of ridges being in a direction perpendicular to the ripple direction. The inventive method and apparatus rely on measuring light-diffraction from ridges in a thin Si film (layer) that are formed as a result of the ELA process. The method offers an indirect measure of the degree of rippling that can be used for monitoring or controlling the ELA process in quasi real-time. In addition, a method is described looking more directly at the ripples themselves, albeit using microscopy techniques that are relatively slow compared to more conventional optical microscopy techniques used for measuring diffraction from ridges.

Ripples are commonly not formed in one direction only. The ripples are predominantly formed in a direction parallel to the scan direction, and also in a direction perpendicular to the scan direction (the line direction). The ripples are periodic and are described herein by the direction of their periodicity, using terminology common in metallurgy, wherein the rolling direction (RD) corresponds with the scanning direction and the transverse direction (TD) corresponds with the line-direction. Accordingly, since ripples oriented in the scan direction are periodic in the transverse direction, they are termed TD ripples. Similarly ripples oriented in the line direction are periodic in the rolling direction and are termed RD ripples.

In accordance with LIPSS theory, TD ripples have a spacing roughly equal to the wavelength of the light, while RD ripples are spaced approximately $\lambda/(1\pm\sin\theta)$, with the $\lambda/(1-\sin\theta)$ spacing typically dominant, wherein $\theta$ is the angle of incidence of laser-radiation on the layer, which in ELA typically is about 5 or more degrees. Ripple formation is instrumental in obtaining uniform poly-Si films, because the grain structure tends to follow the surface periodicity. When ripples are present, ideally, a very ordered film consisting predominantly of rectangular grains sized roughly $\lambda$ by $\lambda/(1-\sin\theta)$ is formed. At lower energy density (ED), grains are smaller and at higher ED, grains are larger. When grains larger than the ripple domain size are grown, herein referred to as super-lateral growth (SLG), surface reflow will result in reduction of the protrusion height and a gradual loss of the order in the film.

In a first experiment to determine a numerical relationship between surface periodicity caused by the ripples and ED of laser pulses, laser scanning microscope (LSM) images of crystallized films were analyzed by fast Fourier transform (FFT), with transforms made in the RD and TD directions. A peak in the FFT indicates the existence of a certain surface periodicity and the location of the peak corresponds to the direction of the surface periodicity. The TD-transform provided sharp peaks at about $1/\lambda$ indicating strong TD periodicity. RD transforms showed peaks less sharp at about (1−sin θ)/λ and with lower amplitude than those of the TD transforms, i.e., less pronounced RD ripples with about (1−sin θ)/λ spacing.

FIG. 1 is a graph schematically illustrating amplitude of corresponding RD and TD transform peaks as a function of energy density (ED) in millijoules per square centimeter (mJ/cm$^2$) in pulses for a total of 25 overlapping pulses in an ELA process. It can be seen that the RD periodicity appears to be greatest at a slightly higher ED than that for which TD periodicity is greatest. Here an OED of about 420 mJ/cm$^2$ is indicated with periodicity in both RD and TD directions decreasing (relatively) sharply with higher ED. It should be noted here that the ED as defined herein is determined using an approach common in industry involving measuring the power in the beam and dividing that by the top hat width of the beam, ignoring any gradients on either side of the top hat.

Figure 2:
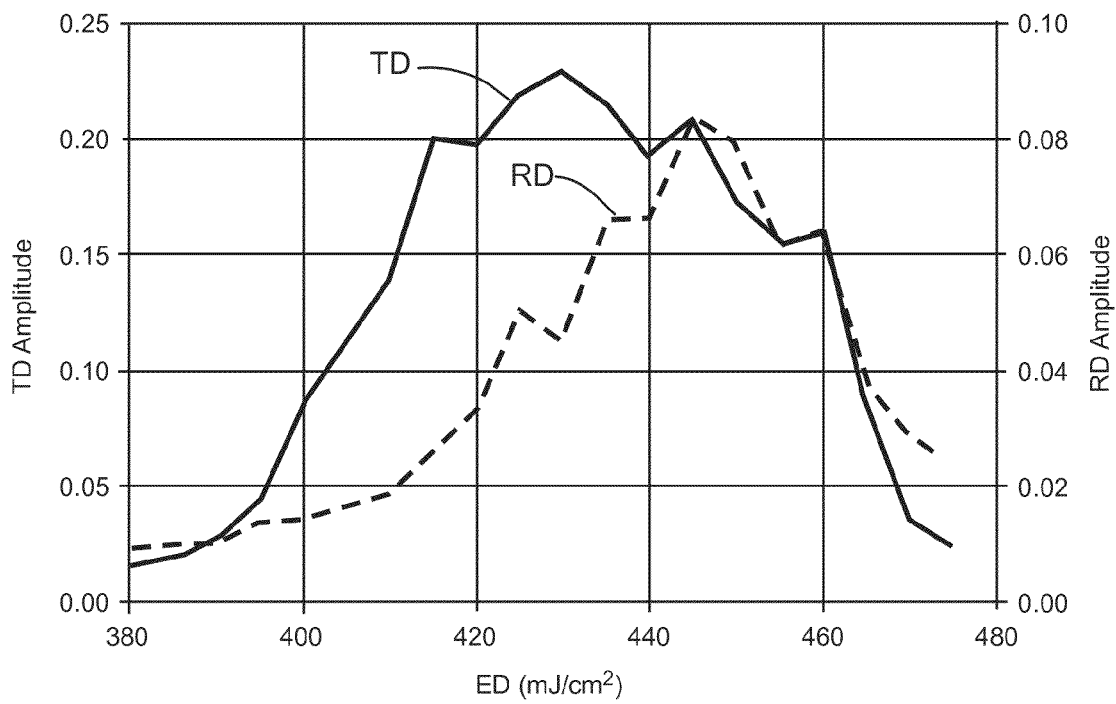
FIG. 2 is a graph schematically illustrating measured peak amplitude as a function of pulse energy density in rolling and transverse directions for FFTs of scanning laser microscope images of A-ELA crystallized silicon layers.

FIG. 2 is a graph similar to the graph of FIG. 1 but for crystallization by an A-ELA process of 25 pulses. Here, the RD ripples show stronger periodicity than for ELA and its peak periodicity is better defined than in the case of the ELA process.

Figure 3:
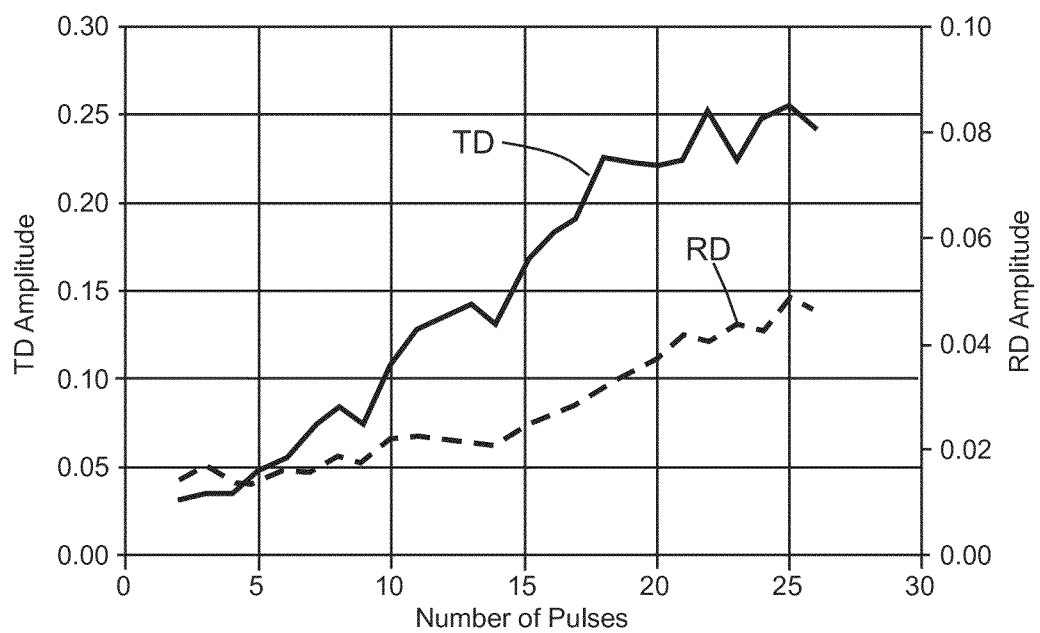
FIG. 3 is a graph schematically illustrating measured peak amplitude as a function of pulse number in rolling and transverse direction for fast Fourier transforms (FFTs) of scanning laser microscope images of A-ELA crystallized silicon layers.

FIG. 3 is a graph schematically illustrating RD and TD peak amplitudes as a function of pulse number at an ED of 420 mJ/cm$^2$, which is somewhat less than the empirically determined OED. It can be seen that periodicity increases steadily in the TD direction up to a pulse number of about 22. In the RD direction, there is very little growth of periodicity until after about 15 pulses have been delivered.

Figure 4:
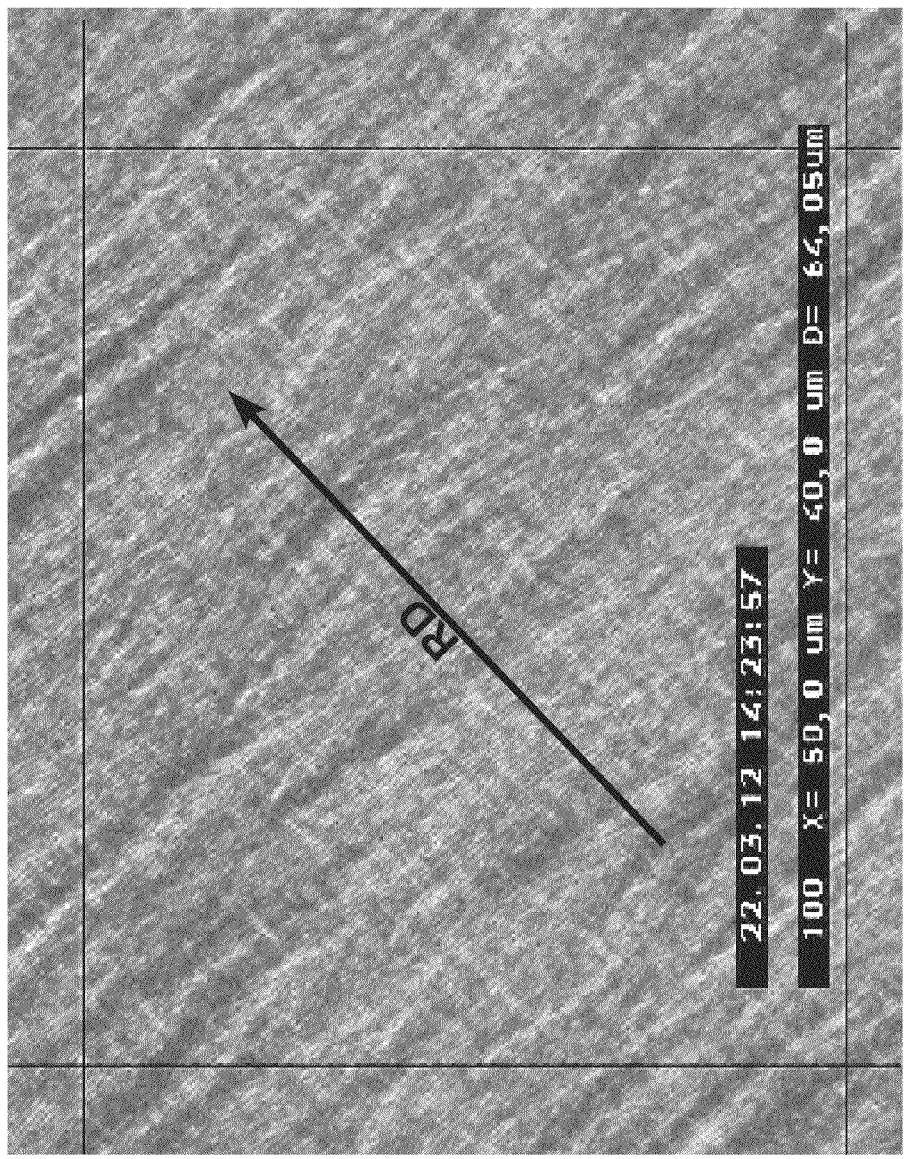
FIG. 4 is a polarized-light microscope image of an area of an ELA crystallized silicon layer illustrating ridges formed transverse to and parallel to the rolling direction (RD) of the layer during crystallization.

FIG. 4 is a polarization microscope image in reflected light. Ridges that are oriented in the transverse direction (which are correlated to ripples in the RD direction, or in other words, following the periodicity based definition, the "TD-ripples") can clearly be seen. Ridges that are oriented in the rolling direction (and correlated to "RD ripples") are less prominent but still evident, as would be expected from the above discussed FFT analysis.

Unlike ripples, the ridges are not strictly periodic. However, the ridges have a characteristic spacing that can typically range between about 1.5 μm and about 3.0 μm, or about an order of magnitude larger than the spacing between the ripples. In accordance with the terminology of ripples the ridges are referred to in the direction of periodicity, i.e., RD ridges are oriented in the transverse direction and TD ridges are oriented in the rolling direction.

The FFT analysis, in itself, clearly provides one means of evaluating a crystallized layer. However, the steps required to generate the above discussed information are generally slow and would not encourage use of such analysis for near real-time on-line monitoring or evaluation of a layer crystallized by ELA or A-ELA. Accordingly, it was decided to investigate the possibility of analyzing diffraction phenomena associated with the perpendicularly oriented groups of ridges associated with RD and TD ripples, rather than attempting to directly measure the ripples themselves.

Figure 5:
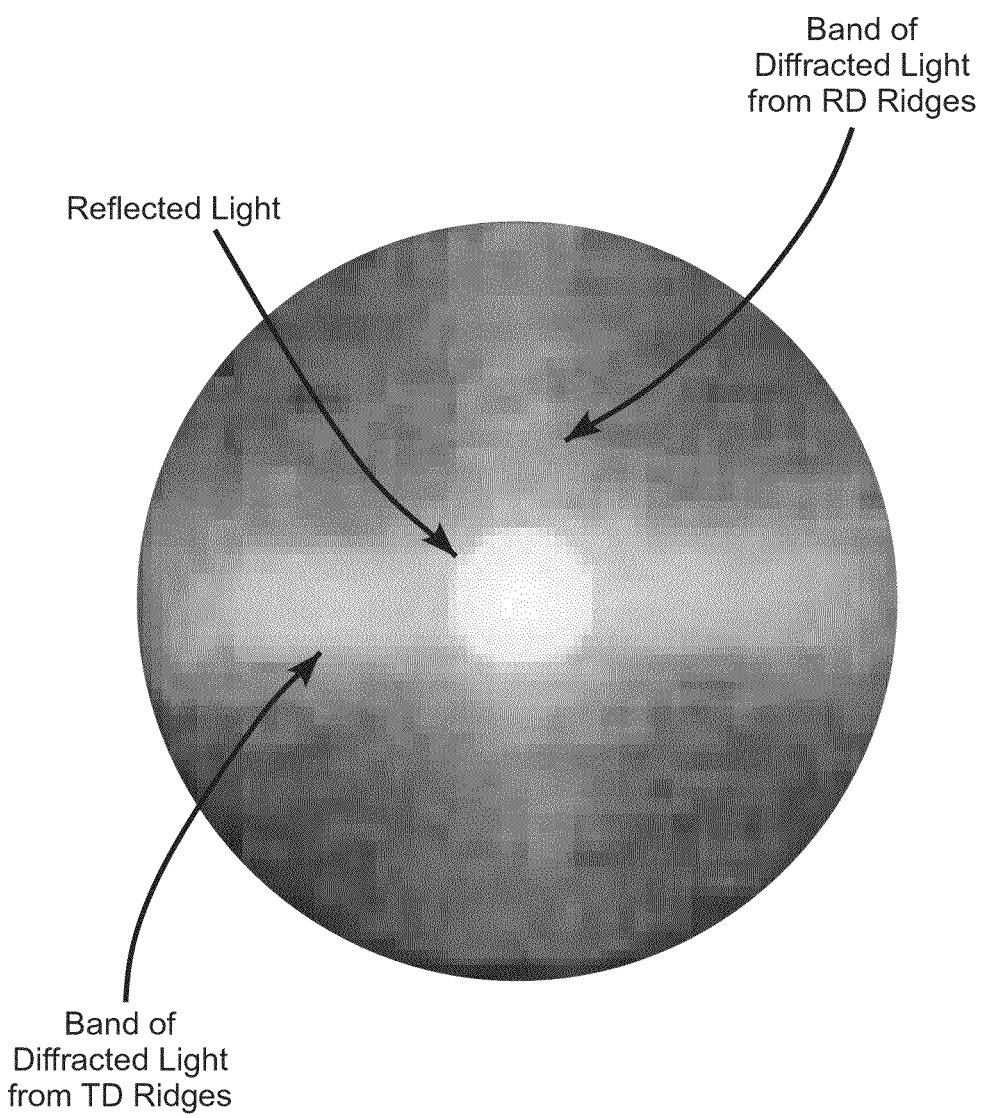
FIG. 5 is a conoscopic microscope image of an area of a crystallized layer similar to that of FIG. 4 depicting horizontal and vertical bands of light formed by diffracted light from respectively transverse-direction and rolling-direction ridges.

FIG. 5 is a conoscopic microscope image of a layer such as that depicted in FIG. 4. This was taken using a commercially available microscope with the eyepiece removed to allow an image of the back focal plane of the objective to be recorded. In this example, the image was recorded with a simple mobile-telephone camera. The microscope was used in a transmitted light configuration. A first polarizer was located in the illumination light path ahead of the sample and a second polarizer (analyzer) was located after the sample with the polarization direction at 90-degrees to that of the first polarizer.

The center of the conoscopic image corresponds to the optical axis of the microscope system and the distance from the optical axis (center spot) corresponds to the angle over which the light travels. Accordingly, the conoscopic image provides information on the direction of light in the microscope.

A condenser diaphragm was set close to a minimum aperture to limit the angular distribution of incident light on the sample and consequently to restrict the image of the aperture to the center of the conoscopic image. The remainder of the image is formed by light diffracted from the TD and RD ridge groups formed by the crystallization. The polarizer and analyzer, together, act to minimize the brightness of the central spot relative to the rest of the image. At 90-degrees relative rotation the two polarizers form a pair of crossing bands of extinction, known as isogyres, in the conoscopic image. By rotating polarizer and analyzer together with respect to the sample, the isogyres can be rotated away from the diffraction bands to minimize extinction of the bands.

The actual image represented in gray-scale in FIG. 5 is a colored image. The horizontal band is a bluish color and the vertical band is a greenish color. The coloring of the bands can be quite uniform and is believed to be indicative of a high diffraction efficiency at those wavelengths and lower diffraction efficiency at other wavelengths. The uniformity of the coloring of the bands is believed to be a result of variable spacing of the ridges. There may be some spectral overlap between the spectra of the horizontal and vertical bands.

The microscope objective was a 20× objective. A fragmented edge of the central spot where the intensity gradient is high gives an indication of the image pixel size. The larger squares in the dark quadrants are an artifact of JPEG image-compression.

In a horizontal direction of the figure there is a strong band of light resulting from diffraction by RD ridges (as related to TD ripples). In the vertical direction of the figure, there is weaker band of light resulting from diffraction by TD ridges (as related to RD ripples). Transmitted light forms a bright spot in the center of the image.

As would be expected from the graphs of FIG. 1 and FIG. 2, as the pulse ED falls below the OED, the relative brightness of the TD-ridge diffraction band relative to the brightness of the RD-ridge diffraction band decreases steeply with decreasing ED. When the pulse ED rises above the OED, the relative brightness of the TD-ridge diffraction band compared to the brightness of the RD-ridge diffraction band remains about the same, but both fall steeply with increasing ED. Measuring the brightness of the diffraction bands thus provides a powerful method of determining whether ED is above or below OED and by how much.

Figure 6:
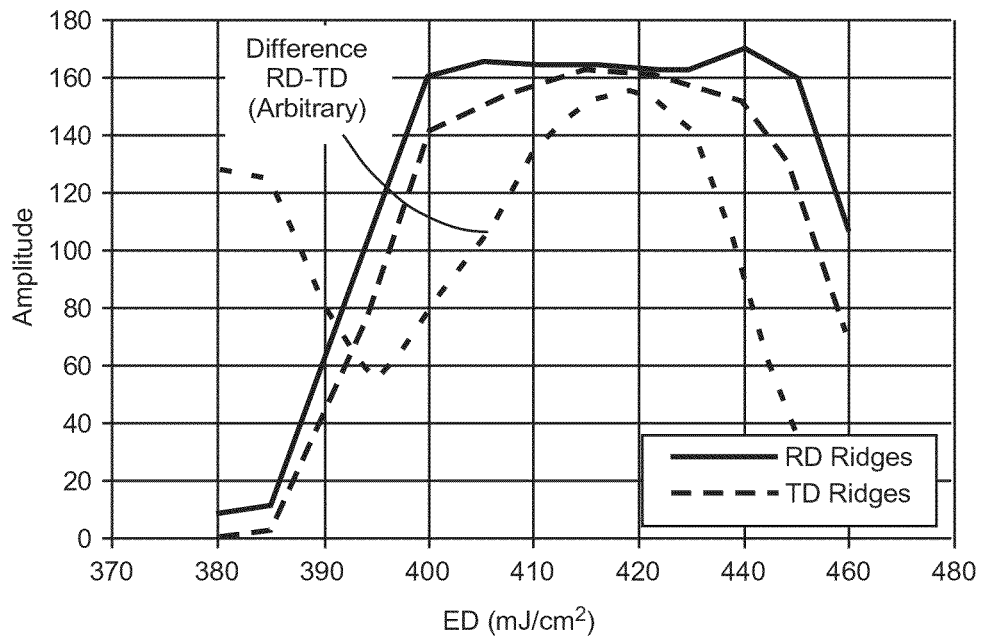
FIG. 6 is a graph schematically illustrating measured amplitude as a function of pulse-energy density for diffracted light from transverse-direction and from rolling-direction ridges of ELA crystallized layers.

FIG. 6 is a graph schematically illustrating RD ridge diffraction intensity (solid curve) and TD ridge diffraction intensity (dashed curve) as a function of pulse ED for a silicon layer area crystallized by 25 overlapping pulses in an ELA process. The intensity of ridges was not measure directly. Instead, a measure for diffraction band intensity was devised based on the observation that the bands have different color and that color information is still present in the regular microscope image.

A commercially available raster graphics editor was used to determine the mean brightness of the blue and green channels of polarized light images as a measure of the diffraction of RD ridges and TD ridges, respectively. A disadvantage of this approach is that the image color channels do not provide optimized filtering to see the band brightness so that there is quite a significant cross-talk between the two signals. Also the signal of the non-diffracted central spot is superimposed on these color channels so that they have a higher noise level. Even so, the difference clearly shows a trend, with the OED found when the ratio of the green channel brightness to the blue channel brightness reaches a maximum, as depicted in FIG. 6 by the dotted curve.

Alternatively a conoscopic image recorded by a CMOS array or CCD array, similar to the image of FIG. 5 can be electronically processed, using appropriate software, to gather measurement data only from the diffraction bands. This has an advantage that the measurement would be insensitive to the actual color and diffraction efficiency of the diffracted light bands in the image, as the spatial information is essentially independent of this. The actual diffraction efficiency may be a function of film thickness and deposition parameters.

Figure 7:
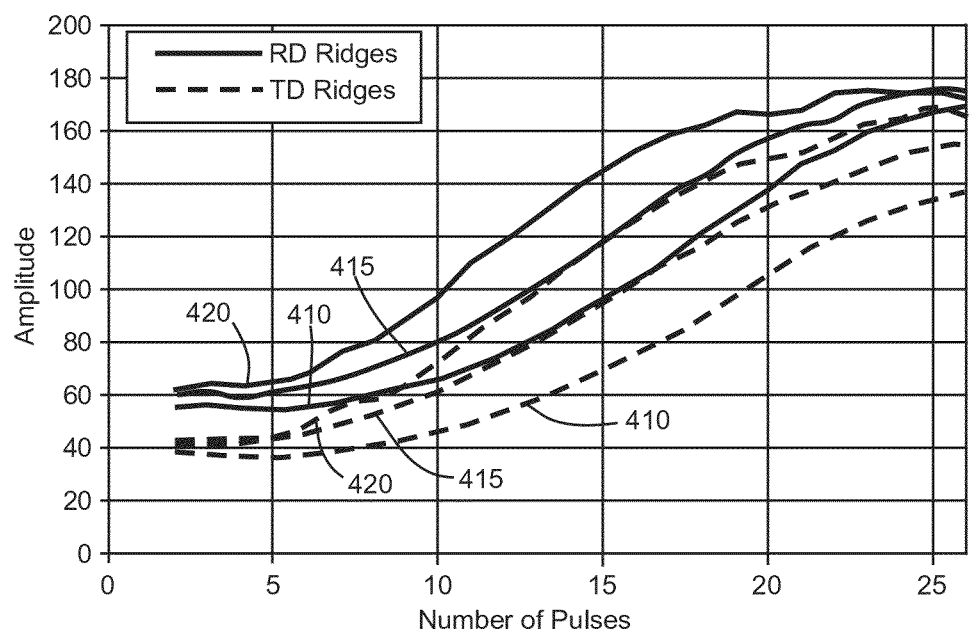
FIG. 7 is a graph schematically illustrating measured amplitude as a function of pulse number for diffracted light from transverse-direction and from rolling-direction ridges of A-ELA crystallized layers for EDs of 410, 415, and 420 mJ/cm$^2$.

FIG. 7 is a graph schematically illustrating RD-ridge diffraction-intensity (solid curves) and TD-ridge diffraction-intensity (dashed curves) as a function of pulse number and ED for pulses sequentially delivered to the same area of a layer being crystallized. The trend here is similar to that of the graph of FIG. 3. The three ED values in each case are 410 mJ/cm$^2$, 415 mJ/cm$^2$, and 420 mJ/cm$^2$, i.e., selected at intervals of little over 1% of the ED. It can be seen that after 15 pulses are deposited the 1% change in ED gives rise to a change of about 20% in signal amplitude. At around 22 pulses, the diffracted signal change is still on the order of 5% or better for the 2% change in ED. This clearly illustrates the sensitivity of the inventive method.

Figure 8:
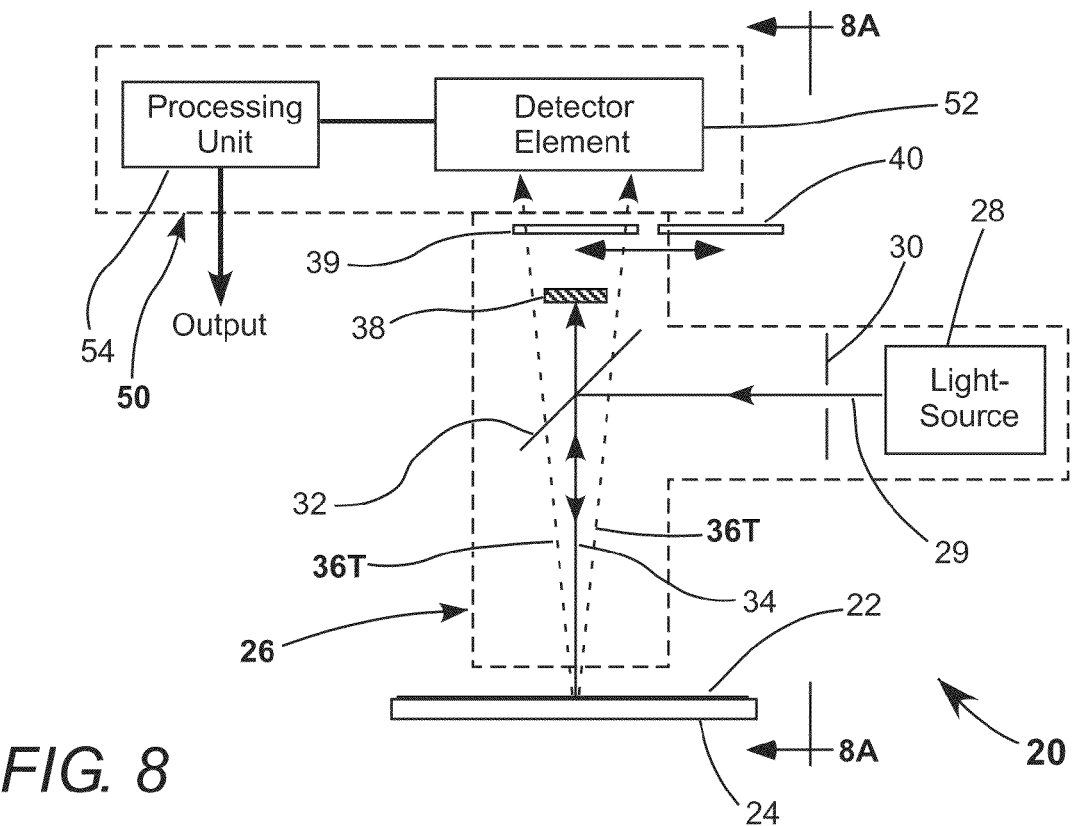
FIGS. 8 and 8A schematically illustrate one preferred embodiment of an apparatus in accordance with the present invention for separately measuring the amplitude of diffracted light from transverse-direction and from rolling-direction ridges of ELA crystallized layers.

FIG. 8 schematically illustrates one preferred embodiment 20 of apparatus in accordance with the present invention for evaluating a crystallized silicon layer. Here a crystallized silicon layer 22 being evaluated is supported on a glass panel 24. A microscope 26 set up for Köhler illumination includes a lamp or light source 28 delivering a beam 29 of white light. A condenser diaphragm 30 provides for control of the numerical aperture of the light cone of beam 29.

Figure 8A:
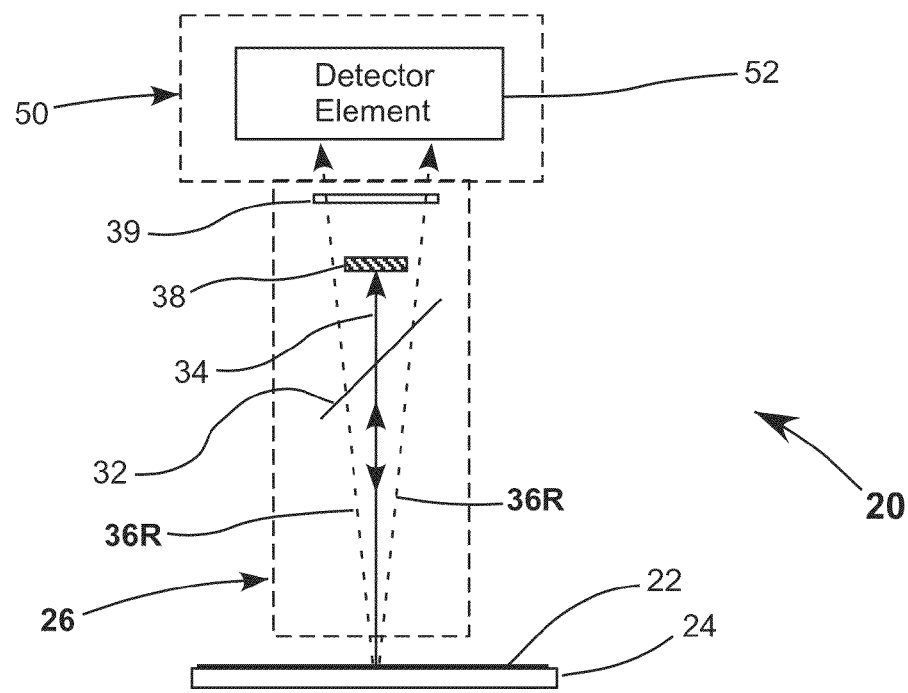

A partially reflective and partially transmissive optical element 32 (a beamsplitter) directs beam 29 onto layer 22 at normal incidence to the layer as depicted in FIG. 8. A portion 34 of the light beam is reflected from layer 22 and portions 36T are diffracted. The suffix T, as used here, means that the light is diffracted by above-described transverse-direction (TD) ridges formed during crystallization of the layer. FIG. 8A depicts apparatus 20 in a plane perpendicular to the plane of FIG. 8 and illustrates light 36R diffracted by above-described rolling-direction (RD) ridges formed during crystallization of the layer.

The reflected and diffracted light is transmitted through element 32. The reflected light is blocked by a stop 38. The diffracted light by-passes stop 38 and is incident on an optical detector element 52 in a detector unit 50. An electronic processor 54 is provided in detector unit 50 and is arranged to determine the amplitude of the diffracted light received by the detector.

Detector element 52 can be a pixelated detector such as a CCD array or a CMOS array as discussed above, recording a conoscopic image of the diffracted light (see FIG. 7) from which the diffracted light intensity can be determined by processor 54 by spatial analysis. Alternatively, the detector element can be a one or more photo-diode elements recording aggregate diffracted light. For this case, optional filter elements 39 and 40 are provided having pass-bands selected to correspond to the particular colors of the TD and RD diffracted light, as discussed above. These can be moved in or out of the diffracted-light path as indicated in FIG. 8 by arrows A.

In either case, another spectral filter (not shown) can be provided for limiting the bandwidth of light from source 28 to those colors which are diffracted. This will reduce noise due to scattered light (not shown) from layer 22, that is able to by-pass stop 38 and mix with the diffracted light.

In FIGS. 8 and 8A optics of microscope 26 including collector lens optics for light source 28, (infinity-corrected) objective optics, and tube lens optics are not shown, for convenience of illustration. Additionally, the microscope can be provided with a Bertrand lens to directly observe the conoscopic image and "eye pieces" (or oculars). The form and function of such optics in a microscope is well known to those familiar with the optical art, and a detailed description thereof is not necessary for understanding principles of the present invention.

Alternative to a reflected light microscope, a transmitted light microscope may be used. Such a microscope setting does not have a beamsplitter but does require a separate condenser lens ahead of the sample. For best results the beam stop 38 may be placed in the back focal plane of the objective or in any conjugate plane thereof after the sample. For reflected light microscopy, the beam stop is best placed in a conjugate plane to the back focal plane of the objective that is located after the beamsplitter so as to not also block the incoming light.

It should be noted that the diffraction from ridges was observed also in the absence of polarizers and/or a beam stop. Diffraction bands could also still be observed after removal of the objective and/or the condenser lenses. Such lenses should thus be seen as a tool to optimize the measurement in terms of brightness and selectivity of the region within the film that is being probed. They are not critical elements of the apparatus described herein.

Figure 9:
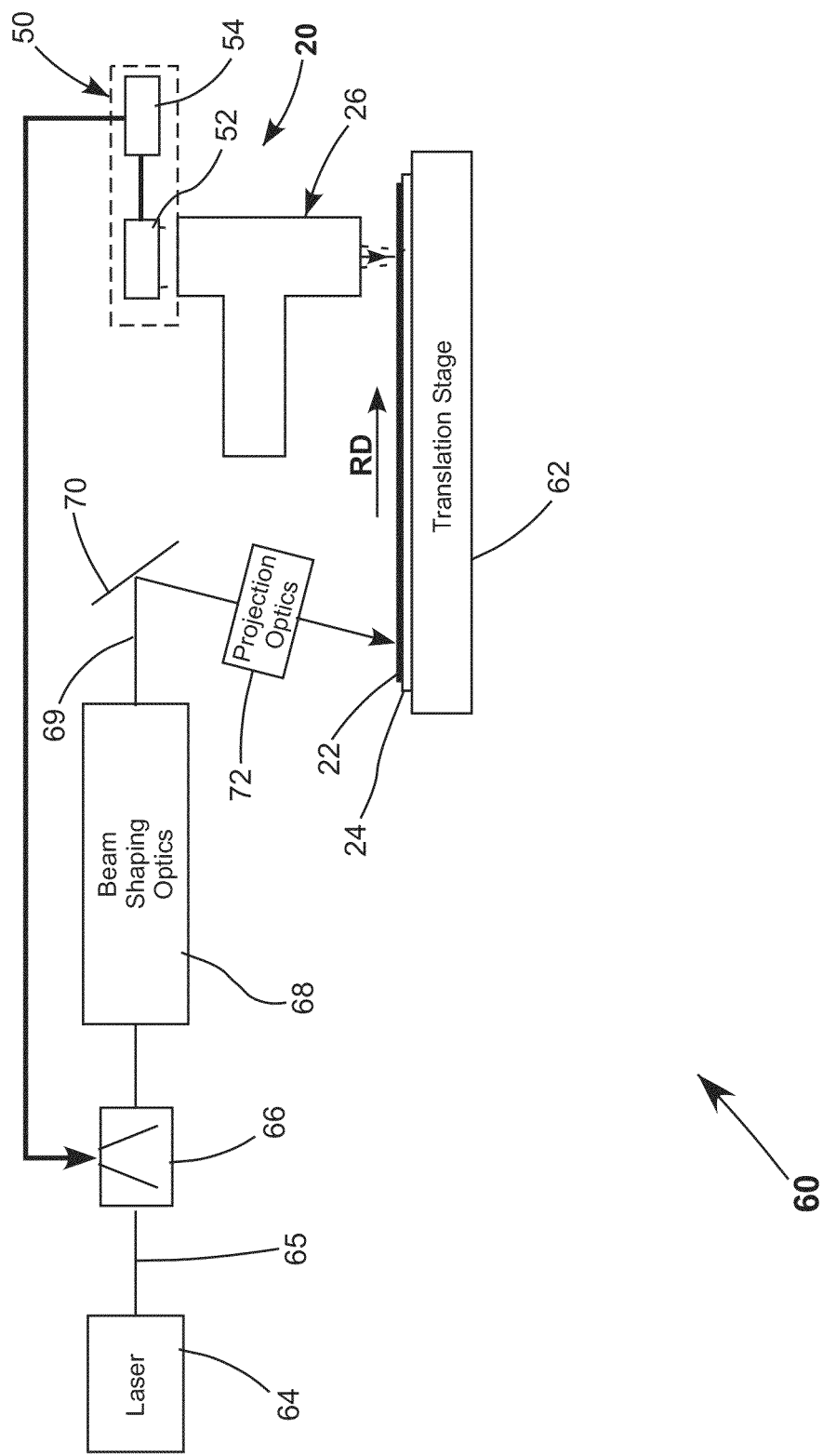
FIG. 9 schematically illustrates one preferred embodiment of ELA apparatus in accordance with the present invention including the apparatus of FIG. 8 cooperative with a variable attenuator for adjusting pulse energy density on a silicon layer responsive to the measured amplitude of diffracted light from transverse-direction and from rolling-direction ridges of the ELA crystallized layer.

FIG. 9 schematically illustrates one preferred embodiment 60 of an excimer laser annealing apparatus in accordance with the present invention. Apparatus 60 includes an excimer laser 64 delivering a laser beam 65. Beam 65 is transmitted through a variable attenuator 66 to beam-shaping optics 68 which deliver a shaped beam 69 via a turning mirror 70 to projection optics 72. The projection optics project the beam onto layer 22 at non-normal incidence as discussed above. Glass panel 24 including layer 22 is supported on a translation stage 62 which moves the layer and panel in a direction RD relative to the projected laser beam.

Above-described apparatus 20 is positioned above layer 22. Processing unit 54 determines from the amplitude of the TD-ridge diffracted and RD ridge diffracted light components observed by detector element 52 and an electronic look-up table created from experimental curves such as the curves of FIG. 6 and FIG. 7 whether the layer has been crystallized with pulses above or below the OED.

Typically the energy density in the projected laser beam (pulse energy or process ED) is initially controlled at the nominal OED. The delivered energy density, however, may drift with time, which is usually recorded as an apparent drift of the OED. If the OED appears to have drifted to a lower value than nominal, the ED will be below the OED; there will be a lower density of ridges in both directions as discussed above; and, accordingly, both the diffraction signals will be reduced in magnitude. A signal is then sent from processing unit 54 to attenuator 66 to reduce the pulse energy delivered to the layer. If the OED appears to have drifted to a higher value than nominal, the ED will be below the instant OED; there will be a lower density of RD ridges relative to TD ridges discussed above; and, accordingly, both the RD ridge diffraction magnitude will decrease while the TD diffraction magnitude remains the same. A signal is then sent from processing unit 54 to attenuator 66 to appropriately increase the pulse energy delivered to the layer.

The above-described correction process does not, of course, have to be done automatically using the feedback arrangement of FIG. 9. Alternatively, processing unit 54 can deliver information concerning the apparent OED drift for display on a monitor to an operator, and the operator can manually adjust the pulse-energy delivered to layer 22.

Figure 10:
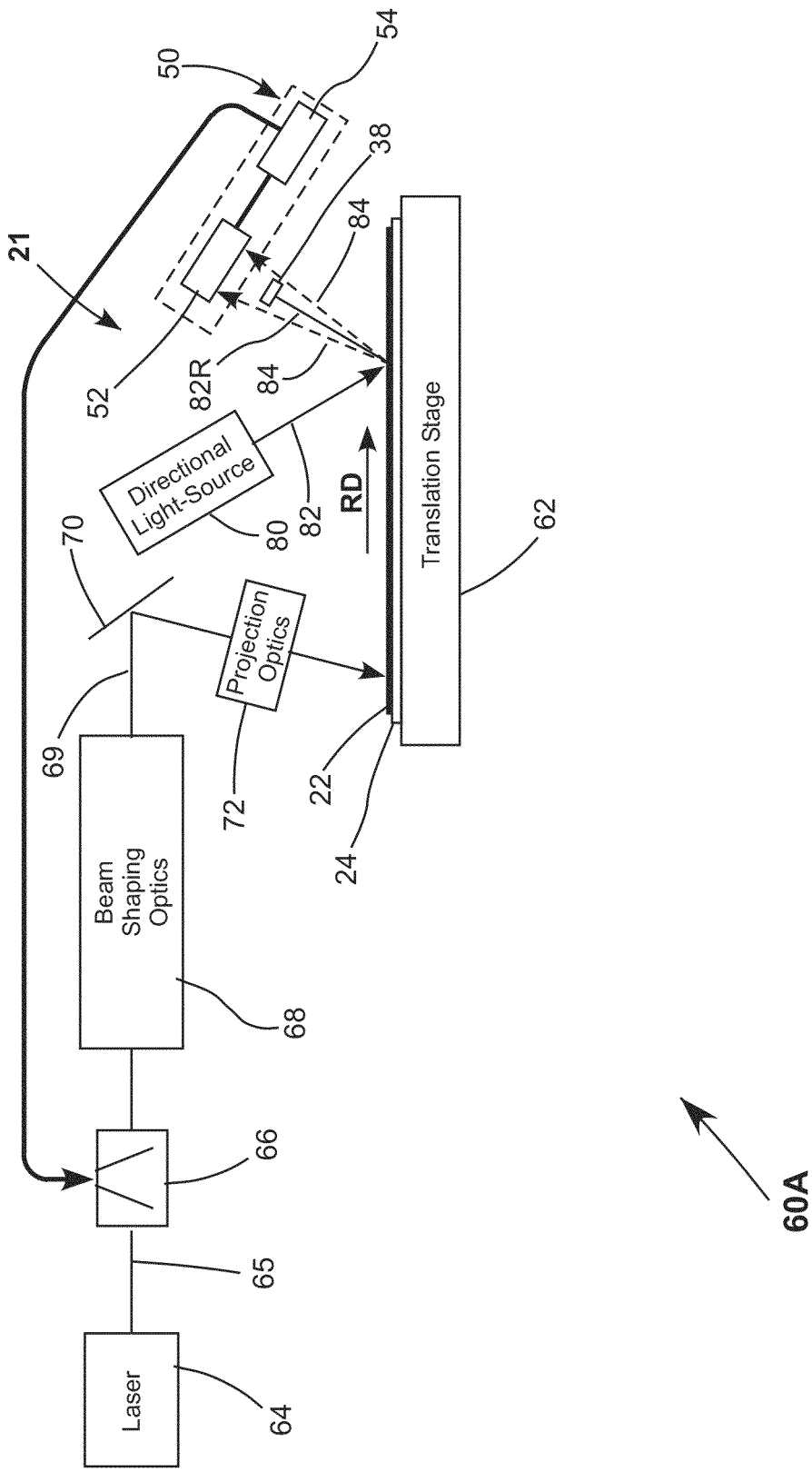
FIG. 10 schematically illustrates another preferred embodiment of an ELA apparatus in accordance with the present invention similar to the apparatus of FIG. 9, but wherein the apparatus of FIG. 8 is replaced by another preferred embodiment of an apparatus in accordance with the present invention for separately measuring the amplitude of diffracted light from transverse-direction and from rolling-direction ridges of the ELA crystallized layer.

FIG. 10 schematically illustrates another preferred embodiment 60A of excimer laser annealing apparatus in accordance with the present invention. Apparatus 60A is similar to apparatus 60 of FIG. 9 with an exception that diffraction measuring apparatus 20 thereof is replaced by an alternative diffraction measuring apparatus 21 which includes a directional light source 80 such as a laser beam 82. The light from the laser is incident on layer 22 at non-normal incidence as depicted in FIG. 10, producing a reflected beam 82R and diffracted light 84. There will be diffracted light beams from TD-ridges and from RD-ridges as described above with reference to apparatus 20 of FIG. 8 and FIG. 9. The reflected beam 82R is optionally blocked by stop 38 and diffracted light is detected by detector element 52 and can be processed by processing unit 54 as described above depending on the form of detector element 52.

The inventive method and apparatus may thus be used to find OED from a panel containing multiple scans each at a different ED for example with ED 10, 5, or even just 2 mJ/cm$^2$ apart. A microscope according to the present invention may be mounted inside an annealing chamber of laser annealing apparatus. The microscope may include a zoom-lens assembly to change the magnification. The panel can be scanned underneath the microscope to allow the panel to be measured at one or multiple locations per condition. The microscope may additionally be provided with a stage to make movements in the transverse direction. An automatic focusing arrangement may be added but this will not be necessary for a conoscopic image as this has a larger depth of focus than the ELA process. Fully crystallized panels can also be measured (either online or offline) in one or more locations to detect the quality of the process so that the crystallization of further panels may be interrupted if necessary. If sufficient measurements are carried out, a map of defects (mura) may be obtained.

In embodiments of the present invention described above, OED is determined from the measured amplitude of light diffracted from a sample in one or each of two directions orthogonal to each other as depicted, for example, in FIG. 6. A potential problem with this method is that changes in measured amplitude can occur for reasons other than a change in ED. By way of example, deterioration of detection components can change the measured amplitude. Further, there may be spatial variations of crystallization over a sample which could yield spatial variations in the measured diffracted amplitude for nominally the same ED of crystallization. Set forth below, beginning with reference to FIG. 11A and FIG. 11B, is a description of an alternative data acquisition and processing method that can reduce, if not altogether eliminate, the above discussed potential problems.

Figure 11B:
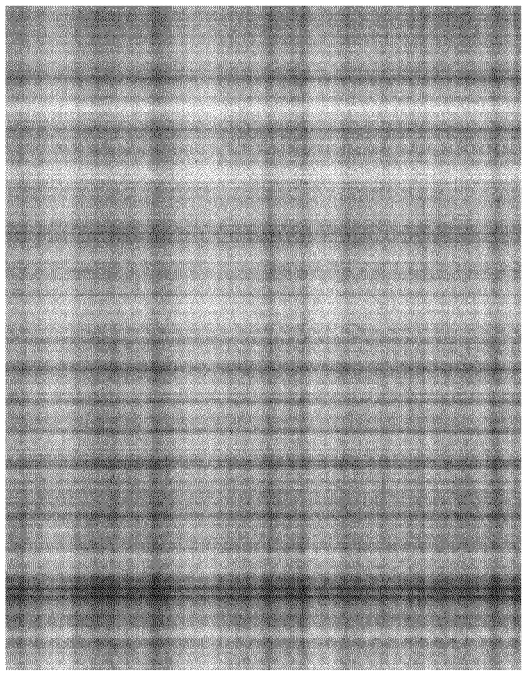
FIG. 11B is a reproduction of a transmission microscope image similar to the image of FIG. 11A but of a silicon layer crystallized at an energy density above the optimum energy density.
Figure 11A:
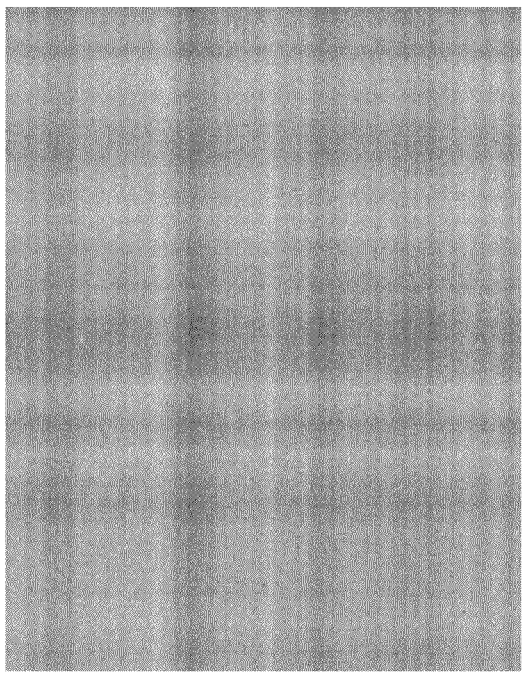
FIG. 11A is a reproduction of transmission microscope image recorded in diffracted light from an area of a silicon layer crystallized at below an optimum energy density (OED) the image including horizontal and vertical periodic features corresponding to rolling-direction and transverse-direction features in the layer.

FIGS. 11A and 11B are micrographs of crystallized samples made by a polarization microscope in transmission. FIG. 11A is made from a silicon layer processed (irradiated) at an ED below OED. FIG. 11B is made from a silicon layer processed with the same laser-beam segment as that of FIG. 11, but at an ED above OED. The microscope objective was a 1.25× objective. Because of this, the images of FIGS. 11A and 11B depict an area greater than that depicted in FIG. 4, the image of which was taken with a 10× objective, and much greater than the images used for creating FIGS. 6 and 7, which were taken with a 20× objective.

The horizontal dimension of the images of FIGS. 11A and 11B is about 9 mm. With such a large field, significant vignetting may occur, with brightness tapering off toward the edges of the image. Software-based flat-field correction was applied to correct for this. The images were filtered to obtain the green channel using a commercially available raster graphics, but blue-filtered images or even unfiltered images have similar appearance. Alternatively, images can be obtained from a microscope supplied with color filters to filter for example only green or only blue light. No condenser diaphragm was used in the microscope illumination. The images have high brightness, and camera shutter time was less than 100 milliseconds (ms).

The images are made in diffracted light with zero-order transmitted light blocked by a polarizer and analyzer at a 90-degree relative rotation. The rotation of the polarizer and analyzer with respect to the sample is such that the isogyres are rotated away from the diffraction band as discussed above. This creates a microscopic image with very high contrast between areas in the layer with a high density of ridges diffracting the light, and areas in the layer with a low density of ridges also diffracting the light.

As discussed above, a difference in ridge density will correspond to a difference in ripple density, and will correspond to a difference in grain structure. Accordingly, the contrast in these images is indicative of a non-uniformity in the layer. Such non-uniformity is commonly referred to as mura. The horizontal stripes in these images are in the scan (rolling) direction and are referred to as scan mura. Scan mura usually appear as a result of slight ED variations along the long-axis of the laser-beam. Such ED variations bring about a local shift of the process window. Accordingly, the scan mura contrasts below and above OED are inverted with respect to each other. The contrast of scan mura stripes is found to be very stable over time, and usually only changes as a result of realignment, contamination, or cleaning of the optics in the beam delivery system of an ELA system. The vertical lines in the images are in the line direction (long-axis of the laser-beam) and are referred to as shot mura. Below OED, shot mura consist mostly of broad stripes, whereas above OED, additionally, sharp stripes are typically observed.

The horizontal and vertical lines can be described as periodic, for purposes of this description and the appended claims, but this does not necessarily mean that the periodicity is regular. Further, the terms horizontal and vertical are used merely for convenience of description of lines perpendicular to each other and do not represent an actual orientation of the lines in practice.

Figure 12:
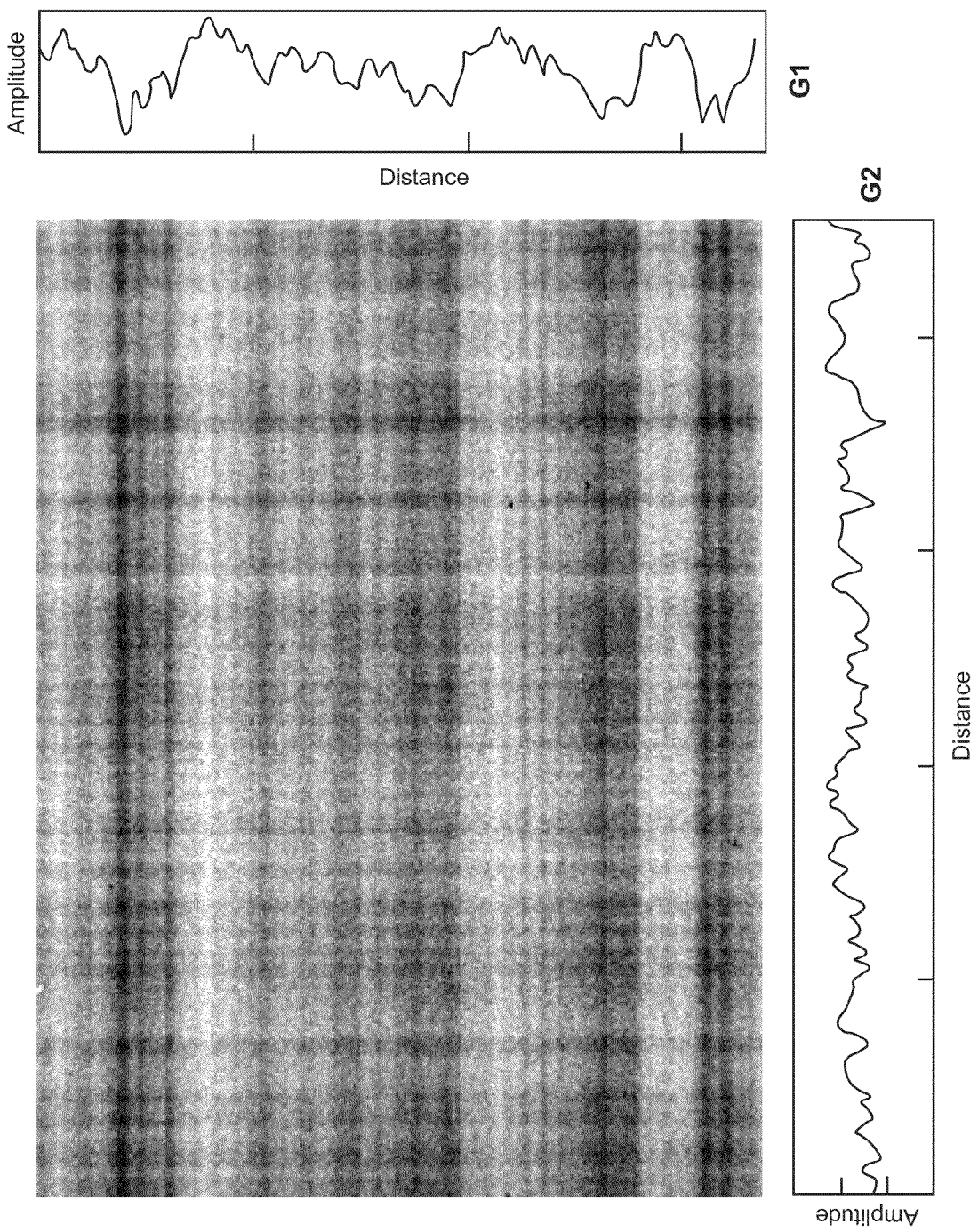
FIG. 12 is a reproduction of a transmission microscope image similar to the image of FIG. 11B and graphs of light amplitude as a function of horizontal and vertical distance from which contrast of the horizontal and vertical features can be measured.

FIG. 12 schematically illustrates how the averaged brightness of columns and rows of image pixels can be taken as a measure of respectively shot mura and scan mura in an image. This is image is taken in a similar ED range as the image of FIG. 11B. Graphs G2 and G1 of FIG. 12 schematically depict measured amplitude of respectively all columns of pixels and all rows of pixels in the image. A contrast value for each can be determined, for example, by subtracting the lowest measure value from the highest measured value in each case, or by taking the standard deviation of amplitude variation around an average amplitude. As noted above, the image in this case was made using a green, software-based filter. This enhances the contrast of scan mura.

Figure 13:
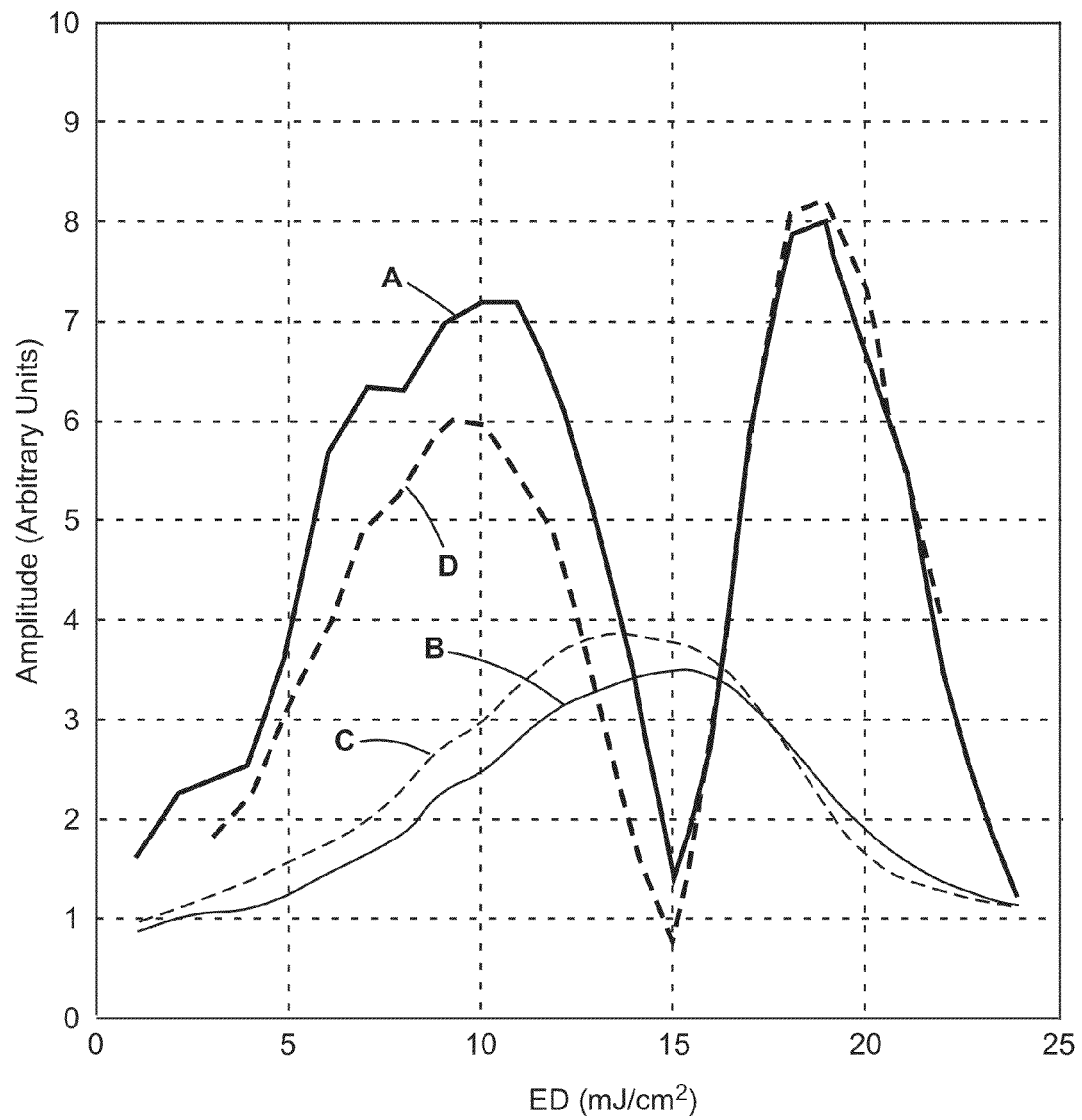
FIG. 13 is a graph schematically illustrating measured contrast in horizontal features of a microscope image similar to the image of FIG. 12, recorded amplitudes of light diffracted from the two groups of layer features as a function of energy density as in the graph of FIG. 2, and the calculated slope of one of the measured amplitudes as a function of energy density.

FIG. 13 is a graph schematically illustrating measured contrast for scan mura (curve A) as a function of ED derived from images such as the image of FIG. 12. This graph is measured from images filtered to show the green channel only. Also schematically depicted for comparison are the measured diffracted light magnitude as a function of ED for the green-channel brightness (curve B) and blue-channel brightness (curve C), of the polarized light microscope images, similar to the curves of FIG. 6; and the absolute value of a calculated slope (curve D) of curve B. It can be seen that the measured contrast (curve A) exhibits a very sharply defined minimum at an ED (the OED) of about 15 mJ/cm$^2$. It can also be seen that the scan mura contrast (curve A) generally follows the form of the calculated slope (curve D) which also exhibits a sharply defined minimum at the same ED as the minimum of curve A.

This is consistent with the observation that scan-mura contrast is largely caused by long-axis energy density variation in the line beam. Such an energy density variation is expected to give a brightness variation according to the relationship depicted by the brightness curve B. Thus, a measurement of scan-mura contrast yields information pertaining to the slope of the ED curve and, through this relationship, the actual processing ED relative to the desired ED or the OED.

Figure 14:
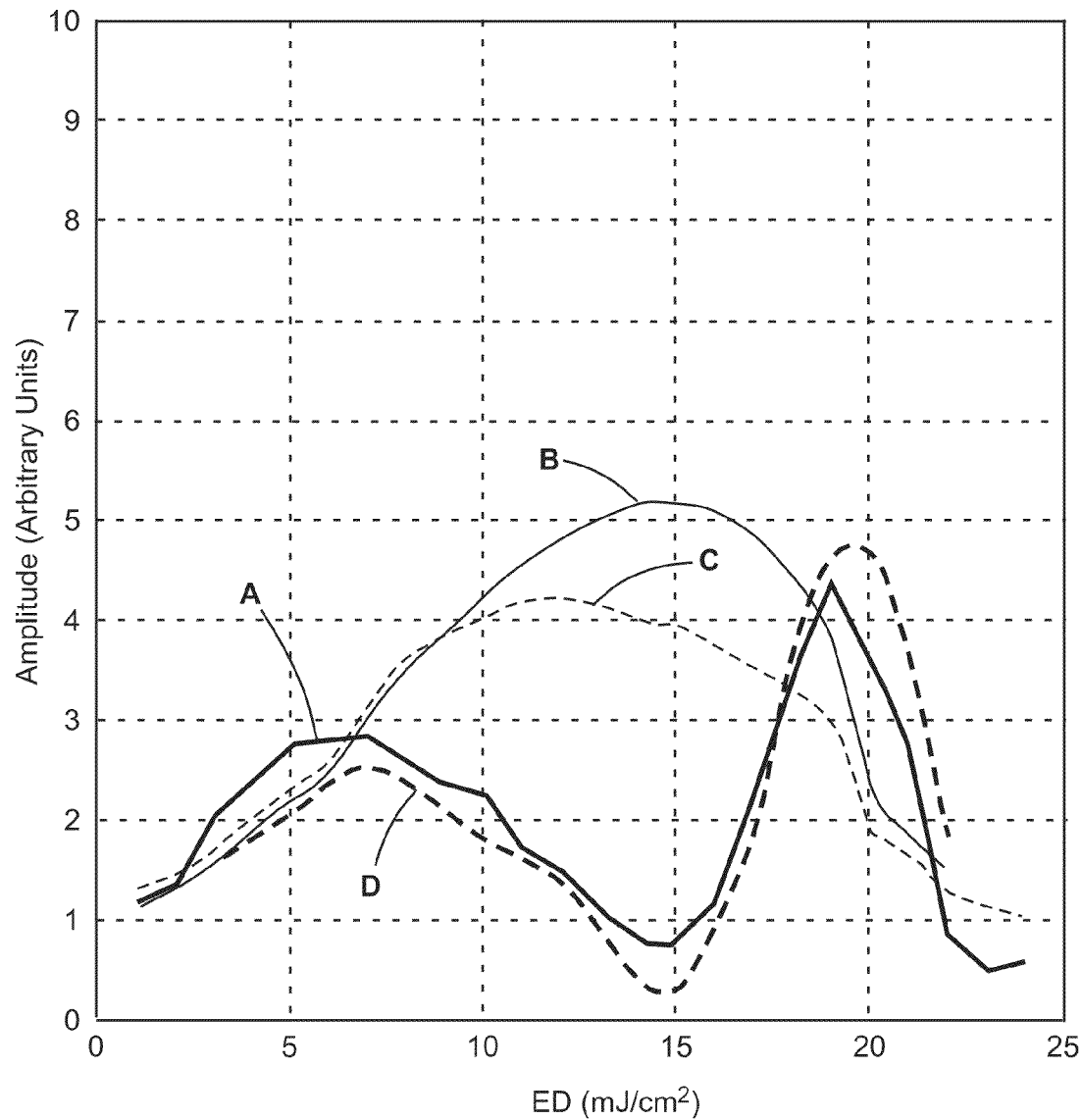
FIG. 14 is a graph similar to the graph of FIG. 13 but wherein the microscope image is from a silicon layer crystallized by a laser crystallization process including a micro-smoothing technique.

FIG. 14 is a graph similar to the graph of FIG. 13 depicting the same measured and calculated quantities discussed above with reference to FIG. 13, but for layers crystallized with the use of micro-smoothing. Micro-smoothing is a technique that is used to reduce the contrast of scan mura stripes. A detailed description of the technique is not necessary for understanding principles of the present invention, and, accordingly, is not presented here. The micro-smoothing technique is described in detail in U.S. Pat. No. 7,723,169, assigned to the assignee of the present invention, and the complete disclosure of which is hereby incorporated herein by reference.

It can be seen by comparing curves A of FIG. 13 and FIG. 14 that the measured contrast is lower, and the minimum of the contrast less well defined, than in the case where micro-smoothing is not used. Nevertheless, a scan mura contrast may be measured that scales faithfully with the slope of the brightness curve as can be seen by comparing curves A and D of FIG. 14. Accordingly, through this relationship, scan-mura contrast may be taken as a measure of the actual processing ED relative to the desired ED or the OED, for above-described monitoring and control of the crystallization process.

It should be noted, here, that above-described polarization microscopy images for contrast measurement may be taken even while a layer on a panel is being ELA processed. During ELA, the panel moves in the scan direction, that is, the exact same direction as the scan-mura stripes. Accordingly, even though the shot-mura contrast may suffer from panel moving during one camera exposure, the scan-mura contrast will not be affected.

Scan-mura contrast is quite stable but can be quite weak. Scan mura contrast may be enhanced by deliberately introducing an optical defect in the beam delivery system, for example a thin metal wire. Such an optical defect will give a shadow and or diffraction stripes in the processed film. As long as the contrast from such optical defect is not to strong, it may again be a measure of the slope of the brightness curve and as such can be used to compensate for ED drift. The area scanned with this segment of the laser beam will have less uniformity and it may be desirable to position it in a location on the panel that is not used for the display active matrix. For example, it may be located at the edge of the panel or at a location where displays panels are later scribed and separated. Alternatively, scan-mura contrast is enhanced by temporarily shutting down of the micro-smoothing. Again, it may be desirable to position the affected area outside the area used for making displays.

It should be noted here that while the present invention is described with reference to evaluating ELA and A-ELA crystallized silicon layers, the invention is applicable to evaluating crystallized layers of other semiconductor materials. By way of example, layers of germanium (Ge), or a Ge and silicon alloy, may be evaluated.

In summary, the present invention is described above with reference to preferred embodiments thereof. The invention is not limited, however, to the embodiments described and depicted herein. Rather the invention is limited only by the claims appended hereto.

What is claimed is:

1. A method for evaluating a semiconductor layer at least partially crystallized by exposure to a plurality of laser-radiation pulses having an energy density on the layer, the crystallization producing a first group of periodic surface features on the layer in a first direction, and a second group of periodic surface features in a second direction perpendicular to the first direction, wherein characteristics of the first and second groups of periodic features depend on the energy density of the laser-radiation pulses to which the semiconductor layer has been exposed, the method comprising:
   illuminating an area of the crystallized semiconductor layer with a beam of light directed normal to the surface of the layer;
   recording an image of the illuminated area with a detector aligned to capture light centered on an axis normal to the layer and arranged to capture light diffracted from the illuminated area by the first and second groups of periodic features, with the variations in brightness within the recorded image corresponding to the characteristics of the first and second groups of periodic features in the illuminated area of the layer; and
   determining the energy density from a measure of the contrast in brightness along at least one direction of the image corresponding to one of the first or second directions of the layer.

2. The method of claim 1, wherein the image is a transmission microscope image.

3. The method of claim 1, wherein the image is formed from rows and columns of pixels and the contrast is determined by measuring the amplitude of one of all rows and all columns of pixels in the image and taking the standard deviation from an average amplitude as a measure of the contrast of the periodic image features.

4. The method of claim 1, wherein the image is formed from rows and columns of pixels and the contrast is determined by measuring the amplitude of one of all rows and all columns of pixels in the image and taking the difference between the highest and lowest measured amplitude as a measure of the contrast of the periodic image features.

5. The method of claim 1, wherein the image is green-filtered image.

6. The method of claim 1, wherein the image is a blue filtered image.

7. The method of claim 1, wherein a minimum of the measured contrast indicates an optimum energy density for the crystallization.

8. The method of claim 1, wherein at least a portion of zero order light is blocked from reaching the detector.

9. The method of claim 8, wherein the zero order light is blocked from reaching the detector using a combination of a polarizer and an analyzer set at 90-degree relative rotation.

10. The method of claim 8, wherein the zero order light is blocked from reaching the detector by a stop positioned along central axis of the captured light.

* * * * *